(12) United States Patent
Shiau et al.

(10) Patent No.: US 12,708,684 B2
(45) Date of Patent: Aug. 18, 2026

(54) SELF-STERILIZING DISPLAY DEVICE

(71) Applicant: Wistron Corporation, New Taipei City (TW)

(72) Inventors: Yi-Hau Shiau, New Taipei City (TW); Yu-Chi Cheng, New Taipei City (TW); Kai-Wei Yang, New Taipei City (TW); An-Ching Yen, New Taipei City (TW); Hsien-Jung Chiou, New Taipei City (TW)

(73) Assignee: WISTRON CORPORATION, New Taipei City (TW)

( * ) Notice: Subject to any disclaimer, the term of this patent is extended or adjusted under 35 U.S.C. 154(b) by 782 days.

(21) Appl. No.: 17/866,629

(22) Filed: Jul. 18, 2022

(65) Prior Publication Data

US 2023/0285609 A1 Sep. 14, 2023

(30) Foreign Application Priority Data

Mar. 10, 2022 (TW) ................................. 111108884

(51) Int. Cl.
*A61L 2/10* (2026.01)
*G02B 6/10* (2006.01)

(52) U.S. Cl.
CPC ................ *A61L 2/10* (2013.01); *G02B 6/102* (2013.01); *A61L 2202/14* (2013.01)

(58) Field of Classification Search
CPC .... A61L 2/10; A61L 2/24; G02B 6/02; G02B 6/0031; G02B 6/0051; G02B 6/0083; G02B 6/0091; G02B 6/0096; G06F 3/041
See application file for complete search history.

(56) References Cited

U.S. PATENT DOCUMENTS 8,999,237 B2 4/2015 Tumanov
9,492,576 B1 11/2016 Cudak et al.
(Continued)

FOREIGN PATENT DOCUMENTS

CN 102284139 A 12/2011
CN 205003635 U 1/2016
(Continued)

OTHER PUBLICATIONS

Examination report dated Sep. 24, 2024, listed in related U.S. Appl. No. 17/847,292 (copy not provided).
(Continued)

*Primary Examiner* — Georgia Y Epps
*Assistant Examiner* — Hsien C Tsai
(74) *Attorney, Agent, or Firm* — McClure, Qualey & Rodack, LLP

(57) ABSTRACT

A self-sterilizing display device is applied to self-sterilizing with a UV light. The self-sterilizing display device includes a display, a light-incident layer, a light source, and a transparent protective layer. The light-incident layer is disposed above the display. The light source is disposed at a periphery of the light-incident layer, and a light-emitting surface of the light source faces to the light-incident layer. The transparent protective layer is disposed between the light-incident layer and the display. Herein, the light source can emit the UV light toward the light-incident layer for sterilizing an outer surface of the self-sterilizing display device by irradiation, and the transparent protective layer can filter out the UV light. Therefore, the surface can be sterilized by UV light, and the UV light can be prevented or reduced from being incident on the display below and damaging the display.

20 Claims, 8 Drawing Sheets

(56) References Cited

U.S. PATENT DOCUMENTS

| | | | | |
|---|---|---|---|---|
| 11,590,250 | B2 | 2/2023 | Takahata | |
| 2003/0102803 | A1 | 6/2003 | Chang | |
| 2011/0109529 | A1 | 5/2011 | Hajjar et al. | |
| 2011/0291995 | A1 | 12/2011 | Shr et al. | |
| 2014/0240981 | A1* | 8/2014 | Weber | G02B 6/0096 362/235 |
| 2015/0109546 | A1 | 4/2015 | Tai et al. | |
| 2021/0181405 | A1* | 6/2021 | Nichol | G02B 6/0085 |
| 2021/0338859 | A1* | 11/2021 | Yu | A61L 2/10 |
| 2022/0057664 | A1* | 2/2022 | Higano | G02F 1/13338 |

FOREIGN PATENT DOCUMENTS

| | | | | |
|---|---|---|---|---|
| CN | 111538442 | A | 8/2020 | |
| CN | 112599017 | A | 4/2021 | |
| CN | 113589586 | A | 11/2021 | |
| CN | 214751218 | U | 11/2021 | |
| EP | 3043244 | A1 | 7/2016 | |
| JP | 2005082777 | A | 3/2005 | |
| JP | 3748989 | B2 | 2/2006 | |
| JP | 2007188719 | A | 7/2007 | |
| JP | 2013048076 | A | 3/2013 | |
| JP | 2013113896 | A | 6/2013 | |
| JP | 2014039876 | A | 3/2014 | |
| JP | 2014083470 | A | 5/2014 | |
| JP | 2015209349 | A | 11/2015 | |
| JP | 2020124281 | A | 8/2020 | |
| KR | 101813077 | | 12/2017 | |
| KR | 101813077 | B1 * | 12/2017 | G06F 3/041 |
| KR | 20180062950 | A | 6/2018 | |
| KR | 20200091133 | A | 7/2020 | |
| TW | I549704 | B | 9/2016 | |
| WO | 2005034066 | A1 | 4/2005 | |

OTHER PUBLICATIONS

Examination report dated Sep. 26, 2022, listed in related Taiwan patent application No. 111108884.

EESR dated May 15, 2023, listed in related European patent application No. 22 191 899.8.

Examination report dated Jun. 27, 2023, listed in related Japan patent application No. 2022-103523.

Examination report dated Jul. 24, 2025, listed in correspondent China patent application No. 202210445797.0.

Examination report dated Jul. 21, 2025, listed in correspondent India patent application No. 202214053963.

Jin-Wook Choi and Jun Hyup Lee, "Selectively UV-Blocking and Visibly Transparent Adhesive Films Embedded with TiO2/PMMA Hybrid Nanoparticles for Displays," Department of Chemical Engineering, Soongsil University, Seoul, Korea, Materials, Multidisciplinary Digital Publishing Institute, Nov. 21, 2020, https://doi.org/10.3390/ma13225273 Title, Abstract, Figure 1b.

Examination report dated Jul. 16, 2025, listed in correspondent China patent application No. 202210444925.X.

Examination report dated May 13, 2025, listed in related U.S. Appl. No. 17/847,292.

Examination report dated Nov. 12, 2025, listed in related China patent application No. 202210444925.X.

* cited by examiner 10
126
Luv
10a
120a
124
120c
130
130a
154
170a
160
110a
124
120
140
160
120b
170
170b
152
114
110
112

SELF-STERILIZING DISPLAY DEVICE

CROSS-REFERENCE TO RELATED APPLICATION

This non-provisional application claims priority under 35 U.S.C. § 119(a) to Patent Application No. 111108884 filed in Taiwan, R.O.C. on Mar. 10, 2022, the entire contents of which are hereby incorporated by reference.

BACKGROUND

Technical Field

The present invention relates to surface sterilization technologies of a display device, and in particular, to a self-sterilizing display device.

Related Art

With the advancement of technology, display devices are no longer just home appliances, but are now widely used in various public places to provide users with relevant information. For example, display devices have been used as information display boards in open spaces such as department stores, various exhibition halls, or various event centers. However, regardless of whether the display device has a touch function or not, the surface of such display device installed in a public place is frequently touched by people, so there is a concern of germ infection. Therefore, the demand for surface sterilization technology of display devices is greatly increased.

The conventional surface sterilization technique of the display device is mainly to continuously emit UV light to sterilize the display device, and allows most of the UV light to undergo total internal reflection within the display device based on the principle of total internal reflection, so that the UV light spreads across the surface of the display device. However, it is necessary for such surface sterilization technique that, the UV light will emit from inside to the outside of the display device only if the surface of the display device is touched by fingers (resulting change in the relative refractive index of the contact point).

SUMMARY

However, experiments have shown that UV light sterilization requires a certain amount of accumulated light to be effective. Therefore, there are still doubts about whether the surface sterilization effect can be achieved in a short time of finger touch. In addition, the UV light will not only emit forward, but also be incident into display components of a display device. The continuous irradiation of the UV light will damage the display components of the display device, thereby reducing the service life of the display device. Moreover, when the finger does not touch the surface of the display device, total internal reflection cannot ensure that the UV light will not leak forward at all. The continuous leakage of UV light will cause damage to human eyes and skin.

In some embodiments, a self-sterilizing display device with the function of UV light sterilization is provided. The self-sterilizing display device includes a display, a light-incident layer, a light source, and a transparent protective layer. The light-incident layer is disposed above the display. The light source is disposed at a periphery of the light-incident layer, and a light-emitting surface of the light source faces to the light-incident layer. The transparent protective layer is disposed between the light-incident layer and the display. Herein, the light source can emit a UV light toward the light-incident layer for sterilizing an outer surface of the self-sterilizing display device by irradiation, and the transparent protective layer can filter out the UV light.

In some embodiments, the self-sterilizing display device may further include a housing and a heat sink. One surface of the heat sink is attached to the light source, and the other surface of the heat sink is attached to a wall surface of the housing.

In some embodiments, the self-sterilizing display device may further include a touch panel disposed above the display.

In some embodiments, the light-incident layer is a light guide plate.

In some embodiments, the self-sterilizing display device may further include a touch panel, and the transparent protective layer may include a first adhesive layer. Herein, the touch panel is disposed above the light-incident layer. A lower surface of the light guide plate is attached to an upper surface of the display by the first adhesive layer, and an upper surface thereof is attached to a lower surface of the touch panel by a second adhesive layer. In addition, a plurality of light-absorbing particles which are configured to absorb the UV light are distributed inside the first adhesive layer.

In some embodiments, the self-sterilizing display device may further include a touch panel, and the transparent protective layer may include a first adhesive layer and a specular reflective layer. Herein, the touch panel is disposed above the light-incident layer. The specular reflective layer is formed on an upper surface of the display. A lower surface of the light guide plate is attached to the specular reflective layer by the first adhesive layer. In addition, a plurality of light-absorbing particles for absorbing UV light are distributed inside the first adhesive layer.

In some embodiments, the lower surface of the light guide plate has a plurality of microstructures arranged in random order.

In some other embodiments, the lower surface of the light guide plate has a plurality of microstructures corresponding to a black matrix configuration of the display.

In some other embodiments, the light-incident layer may be an adhesive layer.

In some embodiments, the self-sterilizing display device may further include a touch panel. Herein, the touch panel is attached to the transparent protective layer by the adhesive layer, and the refractive index of the adhesive layer is greater than the refractive index of a non-patterned region of the touch panel.

In some other embodiments, the light-incident layer may be a hollow spacer layer.

In some embodiments, the self-sterilizing display device may further include a touch panel, and the hollow spacer layer includes a space b and a reflector. Herein, the touch panel is disposed above the hollow spacer layer. The space is between the display and the touch panel, and the reflector and the light source surround the space.

In some embodiments, the self-sterilizing display device may further include a prism disposed above the light-emitting surface of the light source.

In some embodiments, the self-sterilizing display device may further include a touch panel and a light shielding layer. Herein, the touch panel is disposed above the light-incident layer, and the light shielding layer is disposed above the touch panel opposite to the reflector and the light source.

In some embodiments, an upper surface of the touch panel has a plasma coating film transmissible by the UV light. In some embodiments, an upper surface of the light shielding layer may also have a plasma coating film transmissible by the UV light.

In some embodiments, the plasma coating film has a transmittance greater than 60% in a wavelength range of below 380 nm.

In some other embodiments, the light source includes a plurality of light-emitting units located between a plurality of chip-on-film packaging wires of the display.

In some embodiments, the self-sterilizing display device may further include a fluorescent pattern. Herein, the fluorescent pattern is disposed between the light-incident layer and the display, and is excited by the UV light to emit fluorescent light.

In some embodiments, the self-sterilizing display device may further include a drive circuit, a distance sensor, and a controller. Herein, the drive circuit is coupled to the light source, and the controller is coupled to the distance sensor, the drive circuit and the display. The distance sensor can sense the front of the self-sterilizing display device, and the controller activates the drive circuit to drive the light source when the distance sensor senses that there is no one in front of the self-sterilizing display device.

Based on the above, the self-sterilizing display device of any embodiment is suitable for a thin or narrow-bezel display device, and is suitable for use with or without a touch panel. Herein, the self-sterilizing display device utilizes the built-in UV light source to irradiate the light-incident layer with UV light from the inside to the outer surface, thereby achieving comprehensive and strong sterilization of the outer surface of the self-sterilizing display device. In addition, the self-sterilizing display device also avoids or reduces the incidence of UV light to the display below, causing damage to the display, by arranging at least one line of defense below the light-incident layer. In this way, the self-sterilizing display device not only has a self-sterilization function, but also does not significantly reduce the service life of the display due to long-term exposure to UV light.

DETAILED DESCRIPTION

Figures 1, 2:
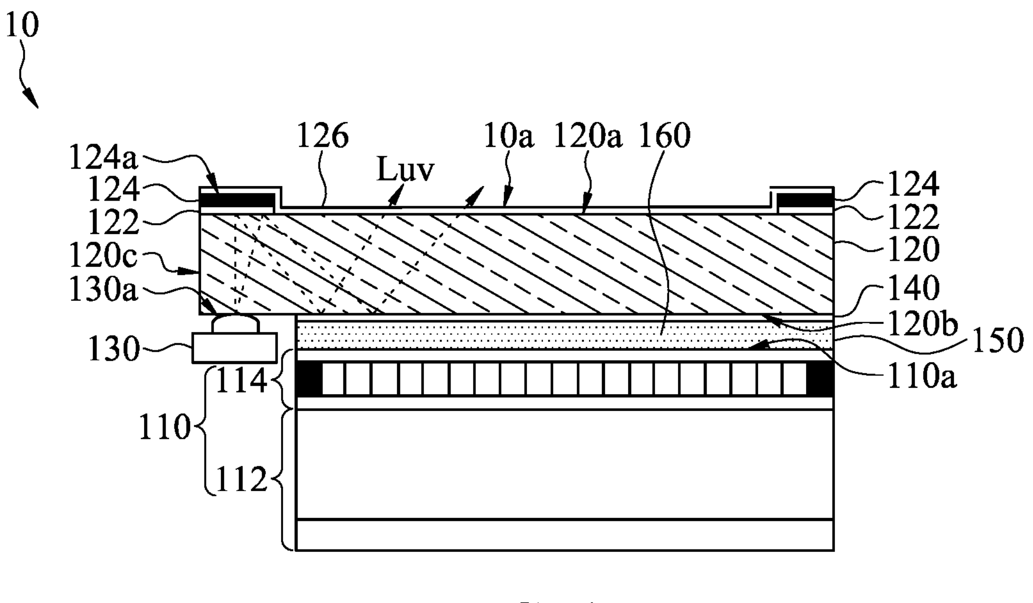
FIG. 1 is a cross sectional view of a self-sterilizing display device according to a first implementation.
FIG. 2 is a cross sectional view of a self-sterilizing display device according to a second implementation.

Referring to FIG. 1, a self-sterilizing display device 10 with the function of UV light Luv sterilization is provided. The self-sterilizing display device 10 includes a display 110, a light-incident layer 120, a light source 130, and a turning layer 140. An outer surface **10*a* of the self-sterilizing display device 10 is sterilized through irradiation by UV light Luv produced by the light source 130. Herein, the display 110 provides a display function of the self-sterilizing display device 10**.

As shown in FIG. 1, the light-incident layer 120 is disposed above the display 110. In this embodiment, the light-incident layer 120 is disposed above a display surface (that is, an upper surface **110*a* shown in FIG. 1) of the display 110, that is, the light-incident layer 120 is located at a position closer to a user viewing the content displayed on the self-sterilizing display device 10. Therefore, the light-incident layer 120 is a transparent material layer that allows visible light to pass through. In some embodiments, the light-incident layer 120 includes an upper surface 120*a*, a lower surface 120*b*, and a plurality of side edges 120*c*, and the side edges 120*c* are coupled between the upper surface 120*a* and the lower surface 120*b***.

The light source 130 is a UV light source 130 that can emit UV light Luv. In an embodiment, the light source 130 is disposed at a periphery of the light-incident layer 120, a light-emitting surface **130*a* of the light source 130 faces to the light-incident layer 120, and the light source 130 can emit UV light Luv toward the light-incident layer 120. The UV light Luv emitted by the light source 130 has a wavelength less than or equal to 380 nm and includes UV light A (UVA), UV light B (UVB), and/or UV light C (UVC). In some embodiments, the light source 130 is a UV light-emitting diode (LED). It is to be understood that, in this specification, at the periphery of a layer refers to near a side edge of the layer, or near an upper surface of the layer close to a side edge thereof, or near a lower surface of the layer close to a side edge thereof. In other words, the light source 130 may be disposed near the side edge 120*c* of the light-incident layer 120, or near the upper surface 120*a* close to the side edge 120*c* of the light-incident layer 120, or near the lower surface 120*b* close to the side edge 120*c* of the light-incident layer 120**.

The turning layer 140 is disposed on the lower surface **120*b* of the light-incident layer 120. The turning layer 140 is configured to change the direction of an optical path of UV light Luv. In other words, in the light-incident layer 120, the UV light Luv with an optical path toward the turning layer 140 can be changed in the direction of the optical path through the turning layer 140 to be toward the upper surface 120*a* of the light-incident layer 120, so that the UV light Luv is emitted from the upper surface 120*a* of the light-incident layer 120 for sterilizing the outer surface 10*a* of the self-sterilizing display device 10 by irradiation. In addition, the turning layer 140 can also avoid or reduce the incidence of UV light Luv to the display 110 below and the damage to the display 110. In some embodiments, the turning layer 140 may be made of a high refractive material. In some embodiments, the turning layer 140 may be formed into a high refractive film on the lower surface 120***b* of the light-incident layer 120 with an inorganic or organic material. In this case, the turning layer 140 is a transparent material. The film may be formed by sputtering, chemical vapor deposition (CVD), spray pyrolysis, or other techniques. In an example, the turning layer 140 may be a complete film. In another example, the turning layer 140 may be a film pattern after patterning.

In some embodiments, the turning layer 140 may be a plasma coating film resistant to UV light Luv. In other words, the plasma coating film can block UV light Luv, that is, has a low transmittance of UV light Luv. For example, the plasma coating film may be an anti-reflection (AR) coating film, an anti-glare (AG) coating film, an anti-smudge (AS) coating film, or an anti-fingerprint (AF) coating film. In some embodiments, the plasma coating film resistant to UV light Luv especially blocks UV light C (UVC). In some embodiments, the plasma coating film resistant to UV light Luv especially blocks UV light C in the wavelength range of 200-280 nm, and has a transmittance less than 65% in the wavelength range of 200-280 nm. In some embodiments, the plasma coating film may be replaced with other optical coating films with similar effect.

In some embodiments, the turning layer 140 adheres to the display 110 by an adhesive layer 150. In other words, a lower surface of the turning layer 140 is adhered to the upper surface 110*a* of the display 110 by the adhesive layer 150. The adhesive layer 150 may be an optical adhesive, such as an optical clear adhesive or an optical clear resin.

In some embodiments, a plurality of light-absorbing particles 160 used for absorbing UV light Luv may be distributed inside the adhesive layer 150. In other words, the light-absorbing particles 160 absorb the UV light Luv incident into the adhesive layer 150, thereby further avoiding or reducing the incidence of UV light Luv to the display 110 below and the damage to the display 110.

In an example, the light source 130 may be disposed above the side edge 120*c* of the light-incident layer 120 and faces to the side edge 120*c* of the light-incident layer 120. Herein, the UV light Luv produced by the light source 130 is incident from the side edge 120*c* of the light-incident layer 120 to the light-incident layer 120.

In some embodiments, the self-sterilizing display device 10 may further include a reflective layer 122. The reflective layer 122 and the light source 130 are disposed opposite to each other on the upper surface 120*a* and the lower surface 120*b* respectively of the light-incident layer 120. For example, the reflective layer 122 is disposed near the side edge 120*c* on the upper surface 120*a*, and the light source 130 is disposed near the side edge 120*c* on the lower surface 120*b* of the light-incident layer 120. In addition, the light-emitting surface 130*a* of the light source 130 faces to the lower surface 120*b* of the light-incident layer 120. The reflective layer 122 can change the direction of an optical path of UV light Luv. In other words, the light source 130 emits UV light Luv toward the reflective layer 122 into the light-incident layer 120, so that the UV light Luv incident into the light-incident layer 120 can be changed in the direction of the optical path through the reflective layer 122 and the turning layer 140 in sequence to emit from the upper surface 120*a* of the light-incident layer 120, for sterilizing the outer surface 10*a* of the self-sterilizing display device 10 by irradiation. Based on this, the self-sterilizing display device 10 may be designed in a narrow bezel, and may also prevent water vapor from directly entering the light source 130. Therefore, the self-sterilizing display device 10 may be suitable for outdoor displays.

In some embodiments, the reflective layer 122 and the light source 130 are disposed in alignment with each other on the upper surface 120*a* and the lower surface 120*b* respectively of the light-incident layer 120. In other words, the reflective layer 122 is disposed on the upper surface 120*a* of the light-incident layer 120 and is close to an edge of the light-incident layer 120. The light source 130 is disposed on the lower surface 120*b* of the light-incident layer 120 and is directly located below the reflective layer 122. In addition, the light-emitting surface 130*a* of the light source 130 faces to the reflective layer 122 through the light-incident layer 120.

In an example, the reflective layer 122 may be a film region only above the light source 130, formed by patterning a film. In another example, the reflective layer 122 may surround the entire edge of the upper surface 120*a* of the light-incident layer 120. In other words, the reflective layer 122 may be a film frame formed by patterning a film.

In some embodiments, the reflective layer 122 may have high reflectance. In some embodiments, the reflective layer 122 may be made of a light shielding material. The light shielding material may be metal such as silver or aluminum.

In some embodiments, the self-sterilizing display device 10 may further include a light shielding layer 124. The light shielding layer 124 is disposed above the reflective layer 122. In other words, the reflective layer 122 is disposed between the light shielding layer 124 and the light-incident layer 120. The light shielding layer 124 can shield edge light leakage and/or underlying metal lines. In this case, the reflective layer 122 can optionally be made of a light shielding material or a transparent material. In some embodiments, the light shielding layer 124 may be a black matrix frame (BM Frame), that is, that being hollow and surrounding the entire edge of the upper surface 120*a* of the light-incident layer 120. In some embodiments, the light shielding layer 124 may be a light shielding material. For example, the light shielding layer 124 may be a frame-shaped pattern formed by screen printing or photolithography using a light shielding material made of carbon black or black pigment mixed with resin.

In some embodiments, the light-incident layer 120 may be a glass plate or a plastic sheet. For example, a glass plate is used as the light-incident layer 120, the lower surface 120*b* of the glass plate is attached to the upper surface of the turning layer 140. The upper surface 120*a* of the glass plate or a plasma coating film 126 thereon is the outer surface 10*a* of the self-sterilizing display device 10. In this case, the self-sterilizing display device 10 is a general display device without the function of touch input.

In some other embodiments, the light-incident layer 120 may be a touch panel. In this case, no light shielding material is disposed at the position of the touch panel opposite to the light source 130. Herein, the self-sterilizing display device 10 is a touch display device with the function of touch input. The touch panel can provide the function of touch input of the self-sterilizing display device 10.

In some embodiments, when the self-sterilizing display device 10 is a touch display device, the light-incident layer 120 may be the entire touch panel (as shown in FIG. 1), or may be a glass plate on top among components of a touch panel 170, or may be a glass plate above the touch panel 170 (as shown in FIG. 2).

In some embodiments, referring to FIG. 2, the self-sterilizing display device 10 may further include a touch panel 170. The touch panel 170 is disposed between the turning layer 140 and the display 110. A lower surface 170*b* of the touch panel 170 is attached to the upper surface 110*a* of the display 110 by an adhesive layer (hereinafter referred to as a first adhesive layer 152). The turning layer 140 is formed on the lower surface 120*b* of the light-incident layer 120. In an example, when the light-incident layer 120 is a glass plate above the touch panel 170, an upper surface 170*a* of the touch panel 170 is attached to the turning layer 140 by another adhesive layer (hereinafter referred to as a second adhesive layer 154). In another example, when the light-incident layer 120 is a glass plate on top among a plurality of components of the touch panel 170 (that is, the light-incident layer 120 is one of the components of the touch panel 170), upper surfaces of the rest of the plurality of components of the touch panel 170 are attached to the turning layer 140 by the second adhesive layer 154. The first adhesive layer 152 and the second adhesive layer 154 may be an optical adhesive, such as OCA or OCR.

In some embodiments, a plurality of light-absorbing particles 160 used for absorbing UV light Luv may be distributed inside the first adhesive layer 152 and/or the second adhesive layer 154. In other words, the light-absorbing particles 160 absorb the UV light Luv incident into the adhesive layer (that is, the first adhesive layer 152/the second adhesive layer 154), thereby further avoiding or reducing the incidence of UV light Luv to the display 110 below and the damage to the display 110. In an example, a plurality of light-absorbing particles 160 may be mixed into the first adhesive layer 152 and the second adhesive layer 154 to absorb the UV light Luv with an optical path toward the display 110. In another example, a plurality of light-absorbing particles 160 may only be mixed into the first adhesive layer 152 to absorb the UV light Luv, and the second adhesive layer 154 is a simple adhesive layer (that is, no light-absorbing particles 160 are distributed inside). In still another example, a plurality of light-absorbing particles 160 may only be mixed into the second adhesive layer 154 to absorb the UV light Luv, and the first adhesive layer 152 is a simple adhesive material (that is, no light-absorbing particles 160 are distributed inside).

In some embodiments, the UV light Luv emitted from the light source 130 is incident from the side edge 120*c* of the light-incident layer 120 to the light-incident layer 120, and in the light-incident layer 120, the UV light Luv incident to the turning layer 140 (that is, incident from the side edge 120*c* of the light-incident layer 120 to the lower surface 120*b* of the light-incident layer 120) can be changed in the direction of the optical path through the turning layer 140 to be toward the upper surface 120*a* of the light-incident layer 120, so that the UV light Luv is emitted from the upper surface 120*a* of the light-incident layer 120 for sterilizing the outer surface 10*a* of the self-sterilizing display device 10 by irradiation. Herein, the light source 130 is adhered to the side edge 120*c* of the light-incident layer 120, and the UV light Luv produced by the light source 130 directly sterilizes the upper surface 120*a* of the light-incident layer 120 through the light-incident layer 120 or sterilizes the upper surface 120*a* of the light-incident layer 120 through the reflection by the turning layer 140. Therefore, the UV light Luv that irradiates the outer surface 10*a* of the self-sterilizing display device 10 has a high intensity and a good sterilization effect.

In some embodiments, the self-sterilizing display device 10 may not provide the reflective layer 122, but directly provide the light shielding layer 124 on the upper surface 120*a* of the light-incident layer 120. In some embodiments, the light shielding layer 124 is formed on the upper surface 120*a* of the light-incident layer 120 and is adjacent to the side edge 120*c* of the light-incident layer 120. Herein, the light shielding layer 124 can shield edge light leakage and/or underlying metal lines. In some embodiments, the light shielding layer 124 may be a BM Frame. In other words, the light shielding layer 124 is hollow and surrounds the entire edge of the upper surface 120*a* of the light-incident layer 120. In some embodiments, the light shielding layer 124 may be a light shielding material. For example, the light shielding layer 124 may be a frame-shaped pattern formed by screen printing or photolithography using a light shielding material made of carbon black or black pigment mixed with resin.

In some embodiments, referring to FIG. 1 or FIG. 2, the upper surface 120*a* of the light-incident layer 120 and an upper surface 124*a* of the light shielding layer 124 have a plasma coating film 126 transmissible by the UV light Luv. In other words, the plasma coating film 126 does not filter out the UV light Luv from the light-incident layer 120, that is, the UV light Luv can be transmitted through the plasma coating film 126. For example, the plasma coating film 126 transmissible by the UV light Luv may be an AR coating film, an AG coating film, an AS coating film, or an AF coating film. In some embodiments, the plasma coating film 126 transmissible by the UV light Luv has a transmittance greater than 60% in a wavelength range of below 380 nm.

Herein, the light-incident layer 120 is a top layer of the self-sterilizing display device 10 (without considering the plasma coating film 126 and the patterned reflective layer 122 and light shielding layer 124). Therefore, the UV light Luv is guided to the outer surface 10*a* of the self-sterilizing display device 10 through the light-incident layer 120 to provide a strong sterilization effect. For example, it is assumed that a 1 cm thick polymethyl methacrylate (PMMA) plastic sheet is used as the light-incident layer 120, and UV light C-light-emitting diode (UVC-LED) is used as the light source 130. The UVC-LED irradiates the outer surface 10*a* of the self-sterilizing display device 10 through the PMMA plastic sheet with the UV light Luv intensity of 1, and can continuously irradiate for about 40 seconds to kill the bacteria on/above the outer surface 10*a* of the self-sterilizing display device 10. When the thickness of the PMMA plastic sheet is reduced to 0.8 cm, the UVC-LED irradiates the outer surface 10*a* of the self-sterilizing display device 10 through the PMMA plastic sheet with the UV light Luv intensity of 5, and can continuously irradiate for about 8 seconds to kill the bacteria on/above the outer surface 10*a* of the self-sterilizing display device 10. When the thickness of the PMMA plastic sheet is reduced to 0.5 cm, the UVC-LED irradiates the outer surface 10*a* of the self-sterilizing display device 10 through the PMMA plastic sheet with the UV light Luv intensity of 8, and can continuously irradiate for about 5 seconds to kill the bacteria on/above the outer surface 10*a* of the self-sterilizing display device 10. In some embodiments, a glass plate is further used as the light-incident layer 120. Because glass hardly absorbs UV light Luv, it can provide the strongest sterilization effect.

Figure 3:
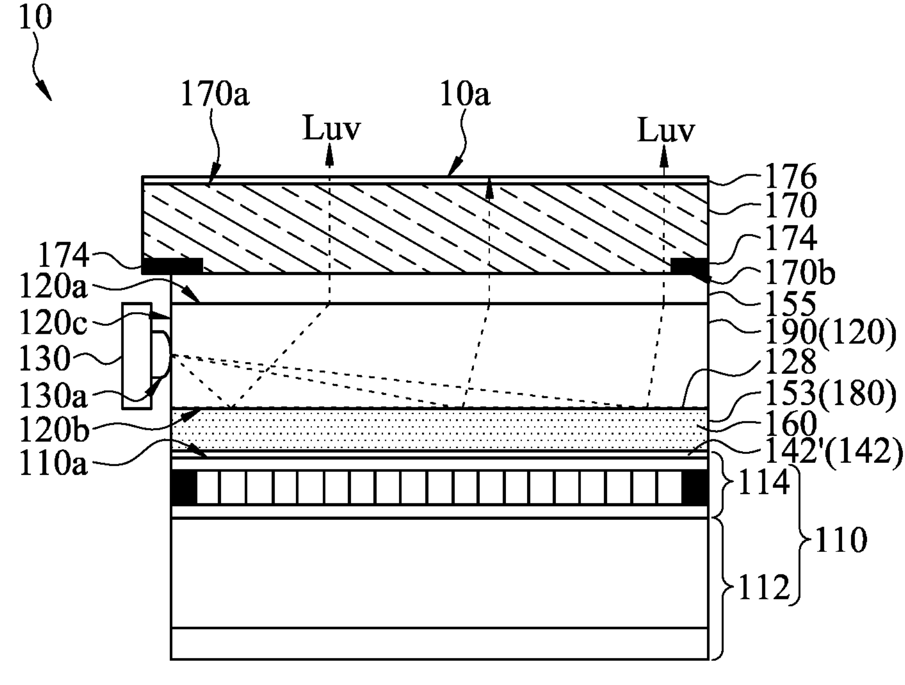
FIG. 3 is a cross sectional view of a self-sterilizing display device according to a third implementation.
Figure 4:
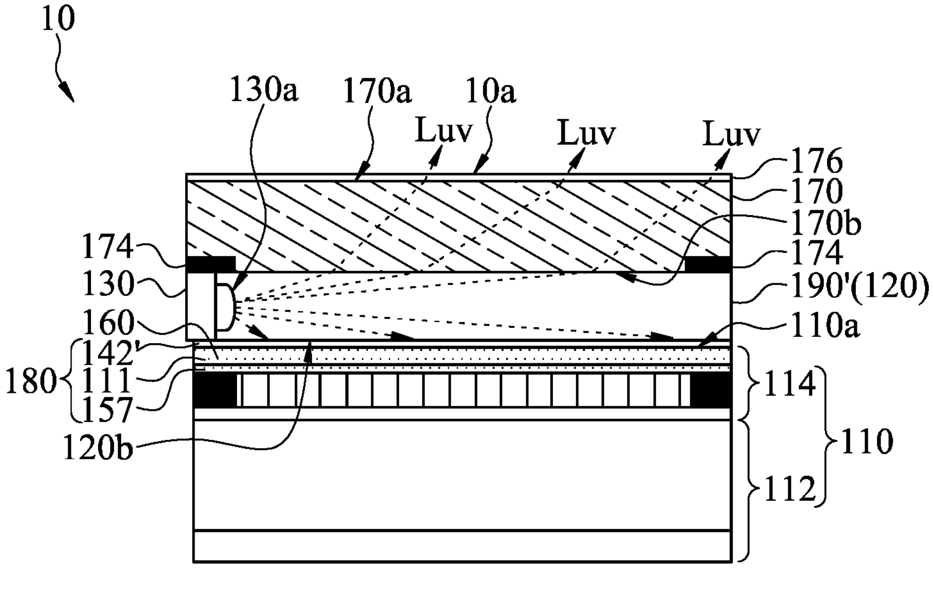
FIG. 4 is a cross sectional view of a self-sterilizing display device according to a fourth implementation.
Figure 5:
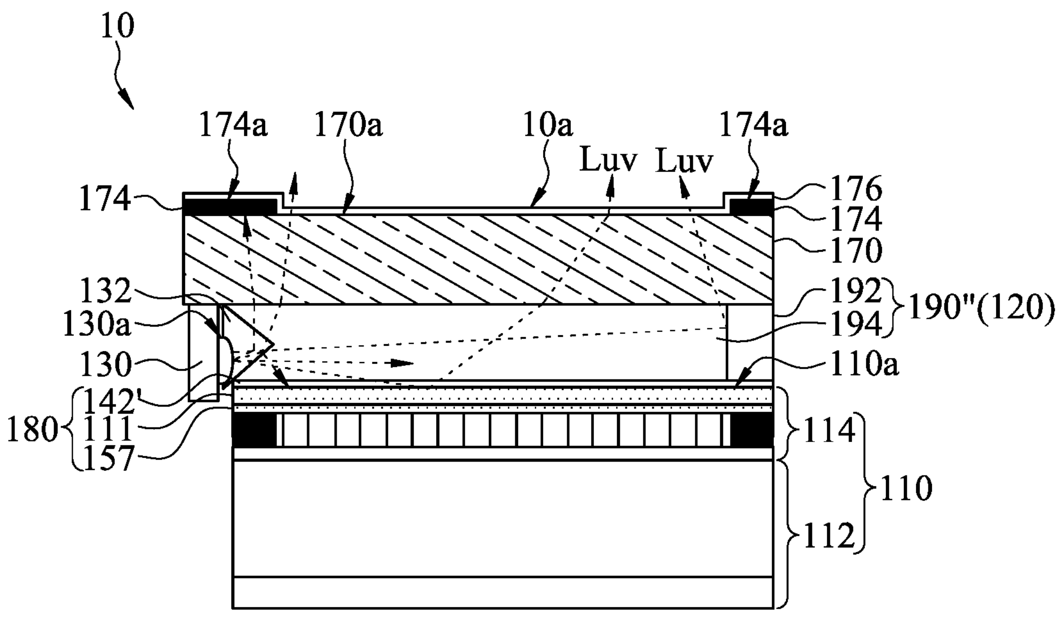
FIG. 5 is a cross sectional view of a self-sterilizing display device according to a fifth implementation.
Figure 6:
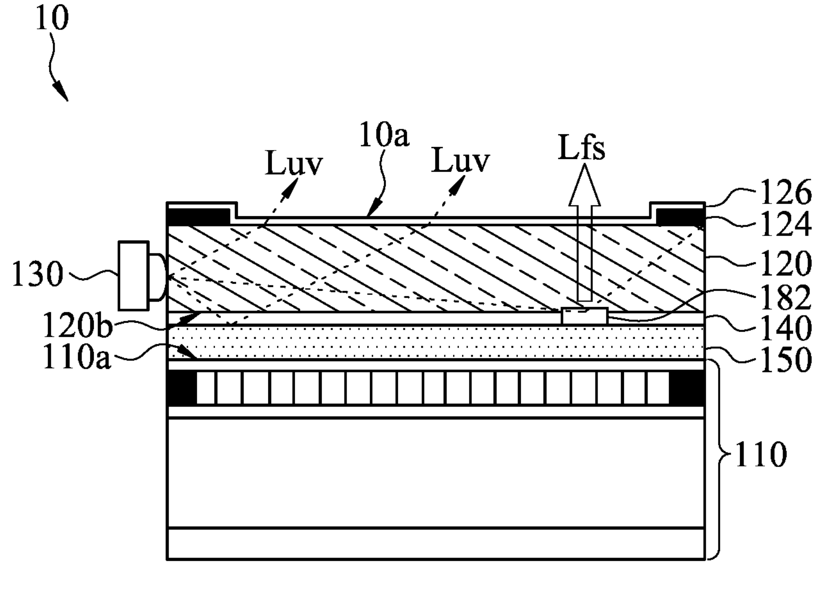
FIG. 6 is a cross sectional view of a self-sterilizing display device according to a sixth implementation.
Figures 7, 8:
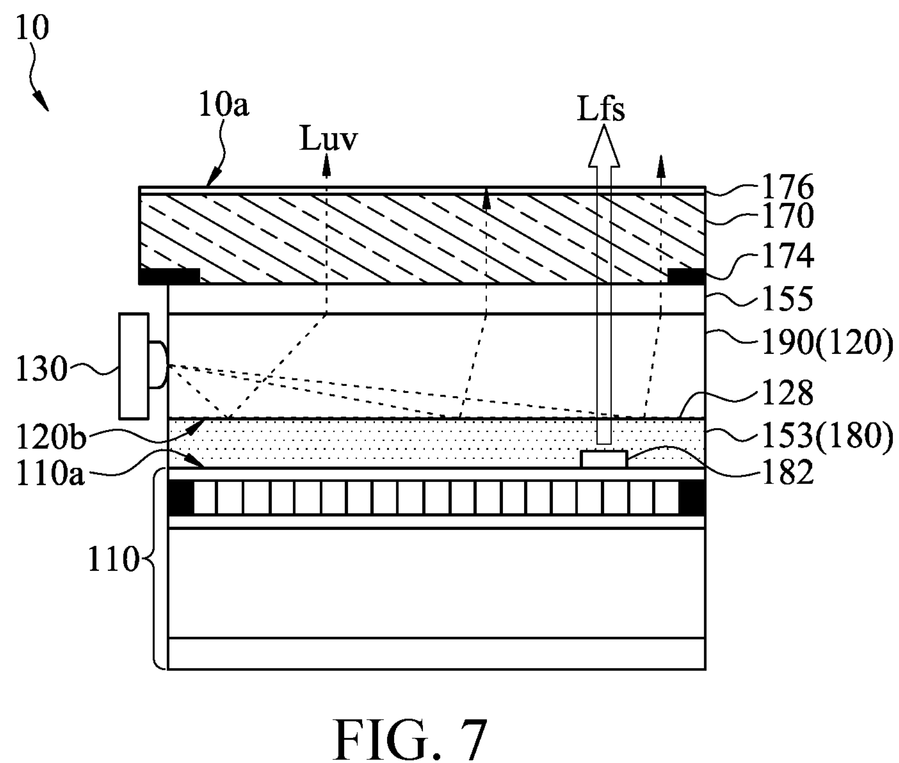
FIG. 7 is a cross sectional view of a self-sterilizing display device according to a seventh implementation.
FIG. 8 is a cross sectional view of a self-sterilizing display device according to an eighth implementation.
Figure 9:
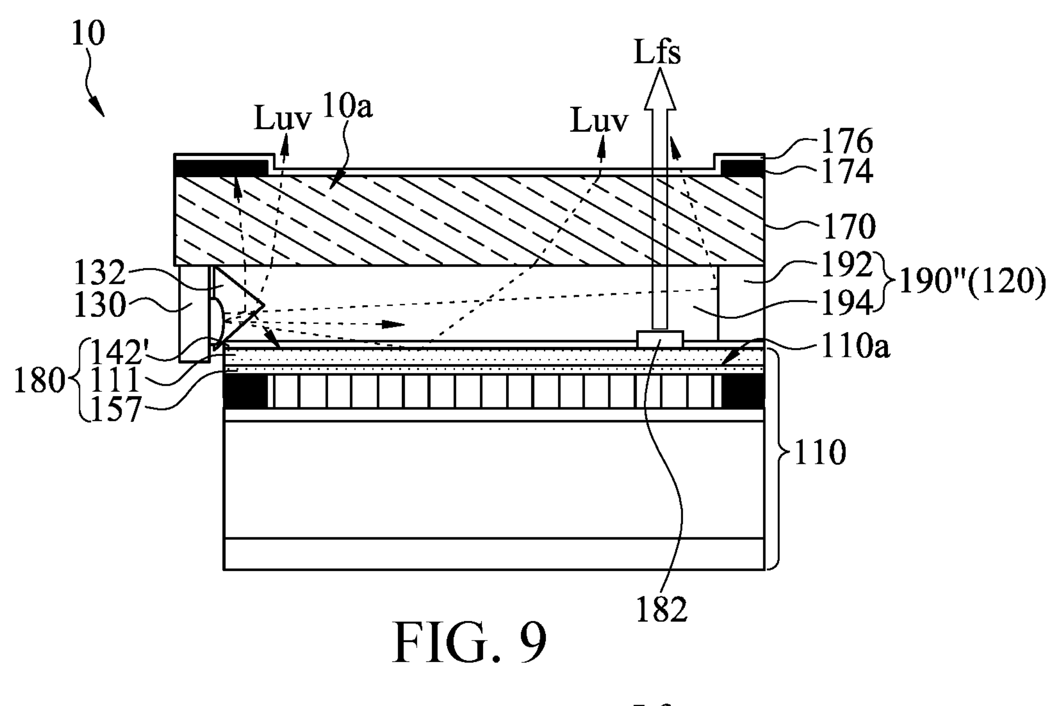
FIG. 9 is a cross sectional view of a self-sterilizing display device according to a ninth implementation.
Figure 10:
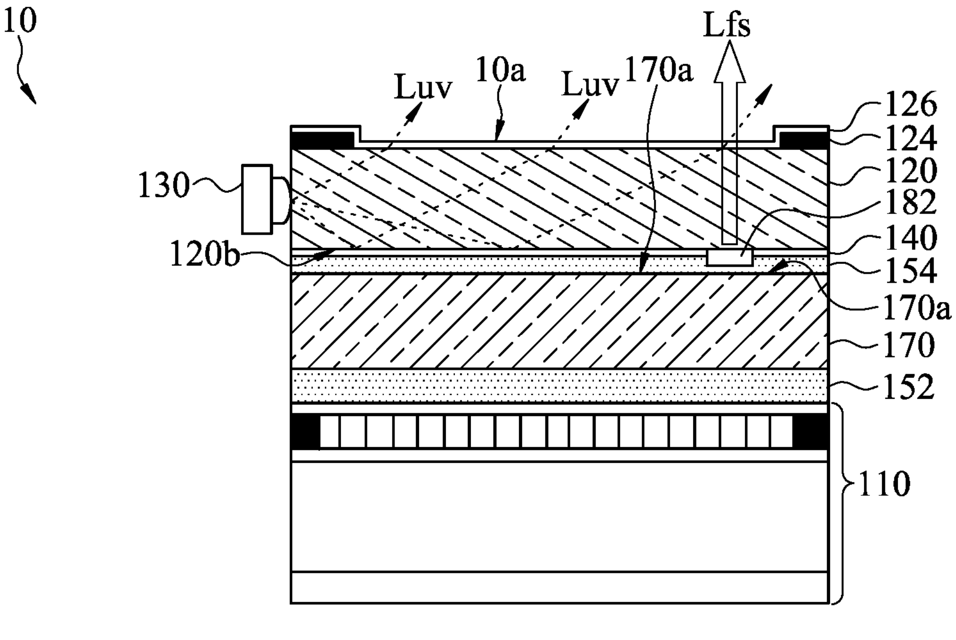
FIG. 10 is a cross sectional view of a self-sterilizing display device according to a tenth implementation.

In some embodiments, when the self-sterilizing display device 10 is a touch display device, the light-incident layer 120 may be the top layer of the self-sterilizing display device 10 (without considering the plasma coating film 126 and the patterned reflective layer 122 and light shielding layer 124), or may be disposed between the touch panel 170 and the display 110, as shown in FIG. 3 to FIG. 5.

In some embodiments, referring to FIG. 3, FIG. 4, or FIG. 5, the self-sterilizing display device 10 may also include a display 110, a light-incident layer 120, a light source 130, a touch panel 170, and a transparent protective layer 180.

The light-incident layer 120 is disposed between the display 110 and the touch panel 170. Herein, the light-incident layer 120 is disposed above a display surface (that is, an upper surface 110*a*) of the display 110. Therefore, the light-incident layer 120 is a transparent material layer that allows visible light to pass through.

The light source 130 is disposed at a periphery of the light-incident layer 120. Herein, the light source 130 is disposed above a side edge 120*c* of the light-incident layer 120, and a light-emitting surface 130*a* of the light source 130 faces to the side edge 120*c* of the light-incident layer 120. The light source 130 can emit UV light Luv toward the light-incident layer 120, and the UV light Luv emitted by the light source 130 is incident from a wall surface of the side edge 120*c* of the light-incident layer 120 into the light-incident layer 120.

The transparent protective layer 180 is disposed between the light-incident layer 120 and the display 110. Herein, the transparent protective layer 180 can filter out the UV light Luv through reflection or absorption, so as to avoid or reduce the incidence of UV light Luv to the display 110 below, thereby preventing the UV light Luv from damaging the display 110.

In other words, after the UV light Luv is incident into the light-incident layer 120, the UV light Luv incident toward the transparent protective layer 180 (that is, incident from the side edge 120*c* of the light-incident layer 120 to a lower surface 120*b* of the light-incident layer 120) can be absorbed or reflected by the transparent protective layer 180 to avoid or reduce the incidence of UV light Luv to the display 110 below and the damage to the display 110. The UV light Luv incident toward the touch panel 170 (that is, incident from the side edge 120*c* of the light-incident layer 120 to an upper surface 120*a* of the light-incident layer 120) can be emitted from the upper surface 120*a* of the light-incident layer 120, and is further transmitted through the touch panel 170 for sterilizing the outer surface 10*a* of the self-sterilizing display device 10 by irradiation.

In some embodiments, the light-incident layer 120 may be a light guide plate 190, as shown in FIG. 3. The light guide plate 190 may be a glass plate, a polystyrene (PS) plastic sheet, a PMMA plastic sheet, a cyclo olefin polymer (COP) plastic sheet, a polycarbonate (PC) plastic sheet, a cyclo olefin copolymer (COC) plastic sheet, a polyethylene terephthalate (PET) plastic sheet, or the like. Preferably, the light-incident layer 120 may be a glass plate or a PS plastic sheet.

In some embodiments, the light-incident layer 120 may be an adhesive layer 190', as shown in FIG. 4. The adhesive layer 190' may be an optical adhesive, such as OCA or OCR. Herein, the adhesive layer 190' has a high refractive index (for example, a refractive index greater than 1.45). In particular, the refractive index of the adhesive layer 190' is greater than the refractive index of a non-patterned region of the touch panel 170, that is, greater than the refractive index the part of the touch panel 170 without indium tin oxide (ITO) lines. Based on this, the UV light Luv emitted by the light source 130 is guided by the high-refractive adhesive layer 190' into oblique light to be incident to the touch panel 170, so as to sterilize the upper surface 170*a* of the touch panel 170 by irradiation.

In some other embodiments, the light-incident layer 120 may be a hollow spacer layer 190", as shown in FIG. 5. In other words, the light-incident layer 120 may maintain a predetermined distance between the display 110 and the touch panel 170 by a spacer (for example, a reflector 192), and a layer of air-filled (dust free or clean) or vacuum space 194 is formed between the display 110 and the touch panel 170, as shown in FIG. 5. Herein, the spacer may simply be used to support the space between the display 110 and the touch panel 170, or may have the functions of supporting and reflecting UV light Luv.

In some embodiments, referring to FIG. 3, using the light guide plate 190 as an example, the transparent protective layer 180 may be an adhesive layer (hereinafter referred to as a first adhesive layer 153). A lower surface 120*b* of the light guide plate 190 is attached to the upper surface 110*a* of the display 110 by the first adhesive layer 153. An upper surface 120*a* of the light guide plate 190 is attached to the lower surface 170*b* of the touch panel 170 by another adhesive layer (hereinafter referred to as a second adhesive layer 155). In addition, a plurality of light-absorbing particles 160 which are used for absorbing UV light Luv are distributed inside the first adhesive layer 153. Based on this, the UV light Luv incident from the side edge 120*c* of the light-incident layer 120 to the lower surface 120*b* of the light-incident layer 120 can be absorbed by the light-absorbing particles 160 inside the first adhesive layer 153 after emitted from the lower surface. Herein, the second adhesive layer 155 does not have a plurality of light-absorbing particles 160 used for absorbing UV light Luv. The first adhesive layer 153 and the second adhesive layer 155 may be an optical adhesive, such as OCA or OCR.

In some embodiments, the transparent protective layer 180 may include the first adhesive layer 153 and a specular reflective layer 142. The specular reflective layer 142 is formed on the upper surface 110*a* of the display 110 (for example, an upper surface of an upper polarizer). The specular reflective layer 142 can reflect UV light Luv to irradiate toward the touch panel 170, so as to block the UV light Luv from entering the display 110. In some embodiments, the specular reflective layer 142 may be a plasma coating film 142' resistant to UV light Luv. In other words, the plasma coating film 142' can block UV light Luv, that is, has a low transmittance of UV light Luv. For example, the plasma coating film 142' may be an AR coating film, an AG coating film, an AS coating film, or an AF coating film. In some embodiments, the plasma coating film 142' resistant to UV light Luv especially blocks UV light C. In some embodiments, the plasma coating film 142' resistant to UV light Luv especially blocks UV light C in the wavelength range of 200-280 nm, and has a transmittance less than 65% in the wavelength range of 200-280 nm.

In some embodiments, a plurality of microstructures 128 may also be formed on the lower surface 120*b* of the light guide plate 190. These microstructures 128 can change the direction of the UV light Luv incident from the side edge 120*c* of the light-incident layer 120 to the lower surface 120*b* of the light-incident layer 120. In addition, by designing these microstructures 128, the UV light Luv incident to the lower surface 120*b* of the light-incident layer 120 can be reflected to the upper surface 120*a* of the light-incident layer 120, that is, the optical path of the UV light Luv is turned from facing the lower surface 120*b* of the light-incident layer 120 to facing the upper surface 120*a* of the light-incident layer 120. In an example, these microstructures 128 may be arranged on the lower surface 120*b* of the light guide plate 190 in random order. In another example, these microstructures 128 may be disposed corresponding to a black matrix of the display 110. Each microstructure 128 may be, for example, a conical groove, a triangular column groove, or a camber groove.

In some embodiments, the size of each microstructure 128 is less than or equal to about one-fifth the size of each pixel of the display 110. In some embodiments, the inner diameter of each microstructure 128 may be about 10-20 μm.

In some embodiments, referring to FIG. 4, using an adhesive layer 190' as an example, the transparent protective layer 180 may include a polarizer 111. The polarizer 111 is a top-most component among a plurality of components of the display 110. The lower surface 170*b* of the touch panel 170 is attached to the upper surface 110*a* of the polarizer 111 by the adhesive layer 190'. A plurality of light-absorbing particles 160 which are used for absorbing UV light Luv are distributed inside the polarizer 111. Therefore, the UV light Luv incident from the adhesive layer 190' to the polarizer 111 can be absorbed by the light-absorbing particles 160 inside the polarizer 111 after emitted from the lower surface 120*b* of the adhesive layer 190', so as to avoid or reduce the incidence of UV light Luv to the display 110 below, thereby preventing the UV light Luv from damaging the display 110. In other words, the polarizer 111 on the display 110 is directly used as a line of defense (that is, the transparent protective layer 180) for preventing UV light from entering the display 110.

In some embodiments, the transparent protective layer 180 may further include a plasma coating film 142' resistant to UV light Luv. The plasma coating film 142' is formed on the upper surface 110*a* of the polarizer 111, and is attached to the lower surface 170*b* of the touch panel 170 by the adhesive layer 190'. The plasma coating film 142' can block UV light Luv, that is, has a low transmittance of UV light Luv, so as to avoid the incidence of UV light Luv to the display 110 and damage to the display 110. In this case, the polarizer 111 may or may not have the light-absorbing particles 160 used for absorbing UV light Luv. For example, the plasma coating film 142' may be an AR coating film, an AG coating film, an AS coating film, or an AF coating film. In some embodiments, the plasma coating film 142' resistant to UV light Luv especially blocks UV light C. In some embodiments, the plasma coating film 142' resistant to UV light Luv especially blocks UV light C in the wavelength range of 200-280 nm, and has a transmittance less than 65% in the wavelength range of 200-280 nm.

In some embodiments, the transparent protective layer 180 may further include another adhesive layer 157. The polarizer 111 adheres to the rest of the plurality of components of the display 110 by another adhesive layer 157, and a plurality of light-absorbing particles 160 used for absorbing UV light Luv are distributed inside the adhesive layer 157. Therefore, the UV light Luv transmitted through the polarizer 111 can be further absorbed by the light-absorbing particles 160 in the adhesive layer 157, so as to avoid or reduce the incidence of UV light Luv to the display 110 below, thereby preventing the UV light Luv from damaging the display 110. In this case, the polarizer 111 may be designed to have or not have the light-absorbing particles 160 for absorbing UV light Luv according to actual requirements. Similarly, the upper surface 110*a* of the polarizer 111 may be designed to directly contact the adhesive layer 190' (that is, no plasma coating film 142' is formed thereon), or may be designed to indirectly contact the adhesive layer 190' (that is, a plasma coating film 142' is formed thereon). The adhesive layer 157 may be an optical adhesive, such as OCA or OCR.

In some embodiments, referring to FIG. 3 or FIG. 4, the light source 130 is disposed opposite to the light shielding layer 174 of the touch panel 170. In an example, the light source 130 is attached below the light shielding layer 174 of the touch panel 170, and the light-emitting surface 130*a* of the light source 130 is fitted with the adhesive layer 190', as shown in FIG. 4.

In some embodiments, referring to FIG. 5, using a hollow spacer layer 190" as an example, the hollow spacer layer 190" may include a space 194 between the display 110 and the touch panel 170, and a reflector 192, and the reflector 192 and the light source 130 surround the space 194. In other words, the reflector 192 and the light source 130 surround a side edge of the hollow spacer layer 190". For example, the reflector 192 may be a frame-shaped reflective plate, and the frame-shaped reflective plate is disposed along an edge of the hollow spacer layer 190". The light source 130 is embedded in the frame-shaped reflective plate, or is disposed above an inner wall of the frame-shaped reflective plate. Based on this, the UV light Luv scattered in the space 194 may be reflected by the reflective plate disposed at the opposite side and/or periphery of the light source 130 to be reused.

In some embodiments, referring to FIG. 5, a prism 132 may be disposed above the light-emitting surface 130*a* of the light source 130. The UV light Luv emitted by the light source 130 is refracted by the prism 132 and then enters the space 194, so that the UV light Luv is scattered in the space 194.

In some embodiments, referring to FIG. 5, the transparent protective layer 180 may include a polarizer 111. The polarizer 111 is a top-most component among a plurality of components of the display 110. The polarizer 111 is disposed at the bottom of the space 194. In other words, the upper surface 110*a* of the polarizer 111 is the lower surface of the hollow spacer layer 190". A plurality of light-absorbing particles 160 which are used for absorbing UV light Luv are distributed inside the polarizer 111. Therefore, after the UV light Luv toward the polarizer 111 in the space 194 is incident to the polarizer 111, the UV light Luv incident to the light-absorbing particles 160 is absorbed by the light-absorbing particles 160. Therefore, the UV light Luv can be prevented or reduced from being incident on the display 110 below, thereby preventing the UV light Luv from damaging the display 110. In other words, the polarizer 111 on the display 110 is directly used as a line of defense (that is, the transparent protective layer 180) for preventing UV light from entering the display 110.

In some embodiments, referring to FIG. 5, the transparent protective layer 180 may further include a plasma coating film 142' resistant to UV light Luv. The plasma coating film 142' is formed on the upper surface 110*a* of the polarizer 111 and is located at the bottom of the space 194. In other words, the upper surface of the plasma coating film 142' is the lower surface of the hollow spacer layer 190". The plasma coating film 142' can block UV light Luv, that is, has a low transmittance of UV light Luv, so as to avoid the incidence of UV light Luv to the display 110 and damage to the display 110. In this case, the polarizer 111 may or may not have the light-absorbing particles 160 for absorbing UV light Luv. For example, the plasma coating film 142' may be an AR coating film, an AG coating film, an AS coating film, or an AF coating film. In some embodiments, the plasma coating film 142' resistant to UV light Luv especially blocks UV light C. In some embodiments, the plasma coating film resistant to UV light Luv especially blocks UV light C in the wavelength range of 200-280 nm, and has a transmittance less than 65% in the wavelength range of 200-280 nm.

In some embodiments, referring to FIG. 5, the transparent protective layer 180 may further include another adhesive layer 157. The polarizer 111 adheres to the rest of the plurality of components of the display 110 by another adhesive layer 157, and a plurality of light-absorbing particles 160 used for absorbing UV light Luv are distributed inside the adhesive layer 157. Therefore, the UV light Luv transmitted through the polarizer 111 can be further absorbed by the light-absorbing particles 160 inside the adhesive layer 157, so as to avoid or reduce the incidence of UV light Luv to the display 110 below, thereby preventing the UV light Luv from damaging the display 110. In this case, the polarizer 111 may be designed to have or not have the light-absorbing particles 160 used for absorbing UV light Luv according to actual requirements. Similarly, the upper surface 110*a* of the polarizer 111 may be designed to directly contact the adhesive layer 190' (that is, no plasma coating film 142' is formed thereon), or may be designed to indirectly contact the adhesive layer 190' (that is, a plasma coating film 142' is formed thereon).

In some embodiments, referring to FIG. 5, the light shielding layer 174 adjacent to the lower surface 170*b* of the touch panel 170 may be disposed above the upper surface 170*a* of the touch panel 170. In other words, the light shielding layer 174 is directly disposed on the upper surface 170*a* of the touch panel 170 along an edge of the touch panel 170. Herein, the light shielding layer 124 can shield edge light leakage and/or underlying metal lines. In this case, the light source 130 is disposed opposite to the light shielding layer 174. For example, the light source 130 is attached on the lower surface 170*b* of the touch panel 170 below the light shielding layer 174, and the light-emitting surface 130*a* of the light source 130 faces the space 194, as shown in FIG. 5. In some embodiments, the light shielding layer 174 may be a BM Frame. In some embodiments, the light shielding layer 174 may be a light shielding material. For example, the light shielding layer 174 may be a frame-shaped pattern formed by screen printing or photolithography using a light shielding material made of carbon black or black pigment mixed with resin.

In some embodiments, referring to FIG. 3, FIG. 4, or FIG. 5, the upper surface 170*a* of the touch panel 170 has a plasma coating film 176 transmissible by the UV light Luv. In other words, the plasma coating film 176 does not filter out the UV light Luv from the light-incident layer 120, that is, the UV light Luv can be transmitted through the plasma coating film 176. For example, the plasma coating film 176 transmissible by the UV light Luv may be an AR coating film, an AG coating film, an AS coating film, or an AF coating film. In some embodiments, the plasma coating film 176 transmissible by the UV light Luv has a transmittance greater than 60% in a wavelength range of below 380 nm.

In some embodiments, the plasma coating film 176 transmissible by the UV light Luv is further formed on an upper surface 174*a* of the light shielding layer 174, as shown in FIG. 5.

In some embodiments, the light-absorbing particles 160 are a UV light absorber, such as phenyl salicylate.

In some embodiments, referring to FIG. 6 to FIG. 10, the self-sterilizing display device 10 may further include a fluorescent pattern 182. The fluorescent pattern 182 is disposed on the lower surface 120*b* of the light-incident layer 120. After the UV light Luv is incident to the light-incident layer 120, the UV light Luv excites the fluorescent pattern 182, so that the fluorescent pattern 182 emits fluorescent light Lfs as a sterilization warning. That is, when the light source 130 emits the UV light Luv, the fluorescent pattern 182 is excited by the UV light Luv and also emits the fluorescent light Lfs toward the outer surface 10*a* of the self-sterilizing display device 10. In this case, a user can know that the self-sterilizing display device 10 is being sterilized by UV light Luv by seeing the fluorescent light Lfs from the outer surface 10*a* of the self-sterilizing display device 10. In some embodiments, the fluorescent pattern 182 may be a prompt text or a prompt graphic. In some embodiments, the fluorescent light Lfs emitted by the fluorescent pattern 182 and the plasma coating films 126/176 are of different color systems, and the fluorescent light Lfs emitted by the fluorescent pattern 182 and the turning layer 140 or the specular reflective layer 142 are also of different color systems. In this case, the contrast of the fluorescent light Lfs can be improved, so that the fluorescent light Lfs can be easily seen.

In some examples, the fluorescent pattern 182 may be disposed between the light-incident layer 120 and the display 110. In an example, referring to FIG. 6, a fluorescent material is film-formed on the lower surface 120*b* of the light-incident layer 120 and patterned into a predetermined pattern (such as a predetermined prompt text or a predetermined prompt graphic), that is, the fluorescent pattern 182 is formed on the lower surface 120*b* of the light-incident layer 120, and the lower surface 120*b* of the light-incident layer 120 is adhered to the upper surface 110*a* of the display 110 by an adhesive layer 150. In another example, referring to FIG. 7 and FIG. 8, a fluorescent material is film-formed on the upper surface 110*a* of the display 110 and patterned into a predetermined pattern, that is, the fluorescent pattern 182 is formed on the lower surface 120*b* of the light-incident layer 120, and the lower surface 120*b* of the light-incident layer 120 is adhered to the upper surface 110*a* of the display 110 by an adhesive layer 150. In still another example, referring to FIG. 9, a fluorescent material is film-formed on the upper surface 110*a* of the display 110 and patterned into a predetermined 30 pattern, that is, the fluorescent pattern 182 is formed on the lower surface 120*b* of the light-incident layer 120, and the lower surface 120*b* of the light-incident layer 120 is connected to the upper surface 110*a* of the display 110 by a spacer.

In another example, the fluorescent pattern 182 may be disposed between the light-incident layer 120 and the touch panel 170. In an example, referring to FIG. 10, a fluorescent material is film-formed on the lower surface 120*b* of the light-incident layer 120 and patterned into a predetermined pattern (such as a predetermined prompt text or a predetermined prompt graphic), that is, the fluorescent pattern 182 is formed on the lower surface 120*b* of the light-incident layer 120, and the lower surface 120*b* of the light-incident layer 120 is adhered to the upper surface 170*a* of the touch panel 170 by a second adhesive layer 154.

In some embodiments, the fluorescent material for forming the fluorescent pattern 182 may be an organic fluorescent powder (that is, a fluorescent dye) with an excitation wavelength of 365 nm, an inorganic fluorescent dye with an excitation wavelength of 365 nm, an inorganic fluorescent dye with an excitation wavelength of 254 nm, or an organic fluorescent dye with an excitation wavelength of 254 nm.

In some embodiments, the display 110 may be a self-emissive display, or a non-self-emissive display. The non-self-emissive display may include a backlight module 112 and a display panel 114 stacked in sequence, as shown in FIG. 1 to FIG. 5. A lower surface of the display panel 114 is attached to the backlight module 112, and an upper surface of the display panel 114 is the upper surface 110*a* of the display 110. The non-self-emissive display may be, for example, a liquid-crystal display (LCD) or an electronic paper. The self-emissive display may be, for example, a plasma display panel (PDP), an electroluminescence (EL) display, a light-emitting diode (LED) display, or a vacuum fluorescent display (VFD).

Figure 11:
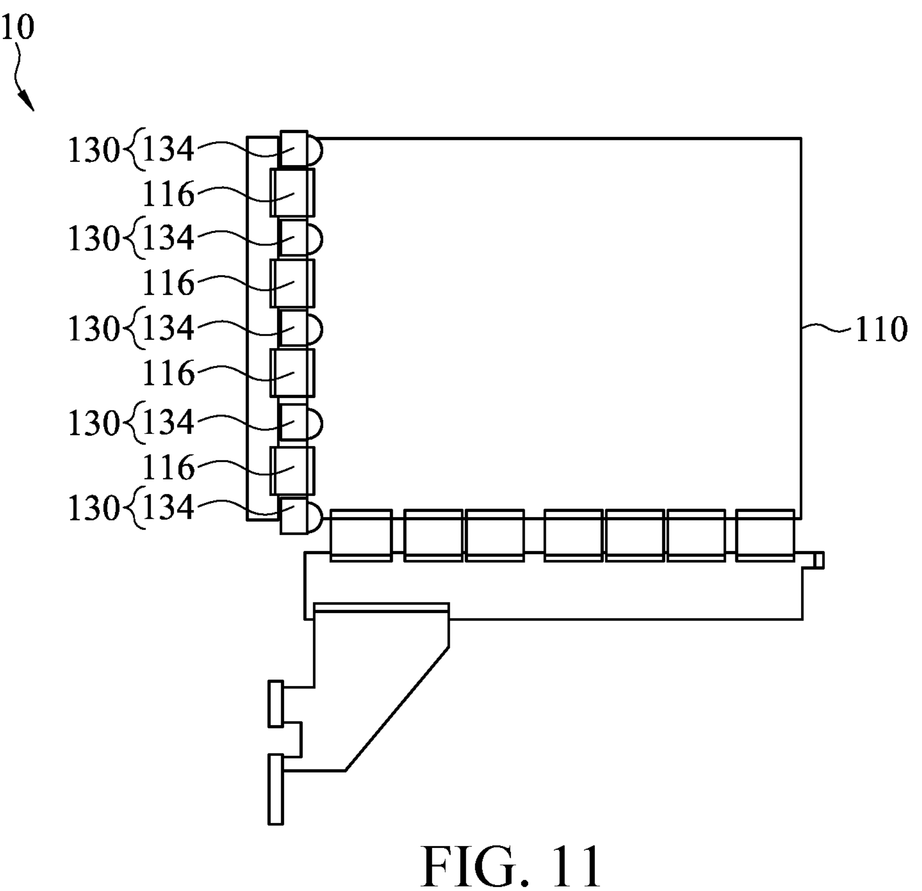
FIG. 11 is a top view of a display of a self-sterilizing display device according to some implementations.
Figure 12:
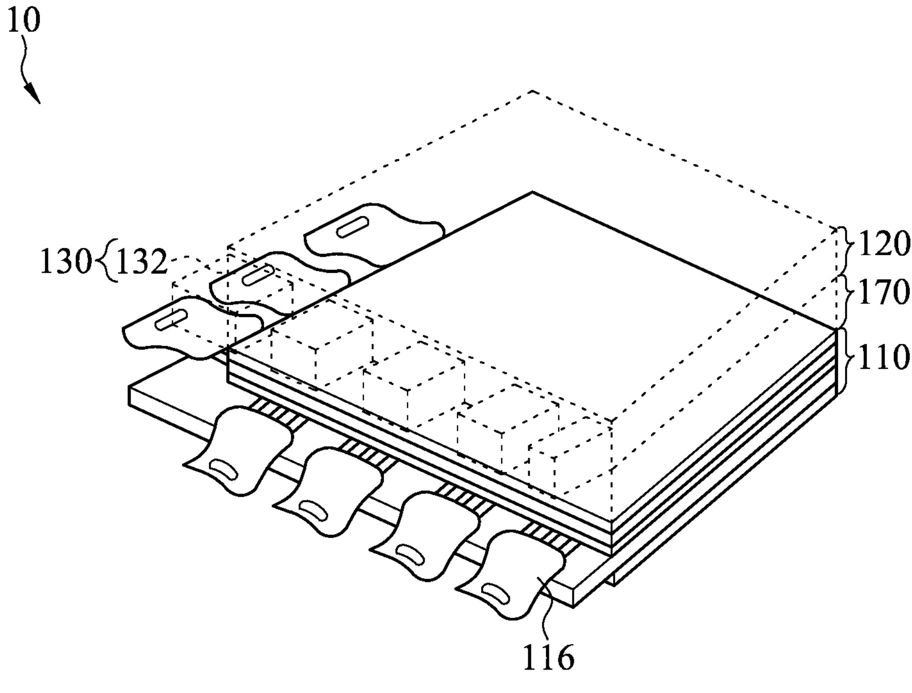
FIG. 12 is a schematic three-dimensional diagram of the self-sterilizing display device in FIG. 11.

In some embodiments, the light source 130 may include a plurality of light-emitting units 134 located between the chip-on-film (COF) packaging wires 116 of the display 110, as shown in FIG. 11 and FIG. 12. In some embodiments, each light-emitting unit 134 may be implemented by one or more LEDs.

Figure 13:
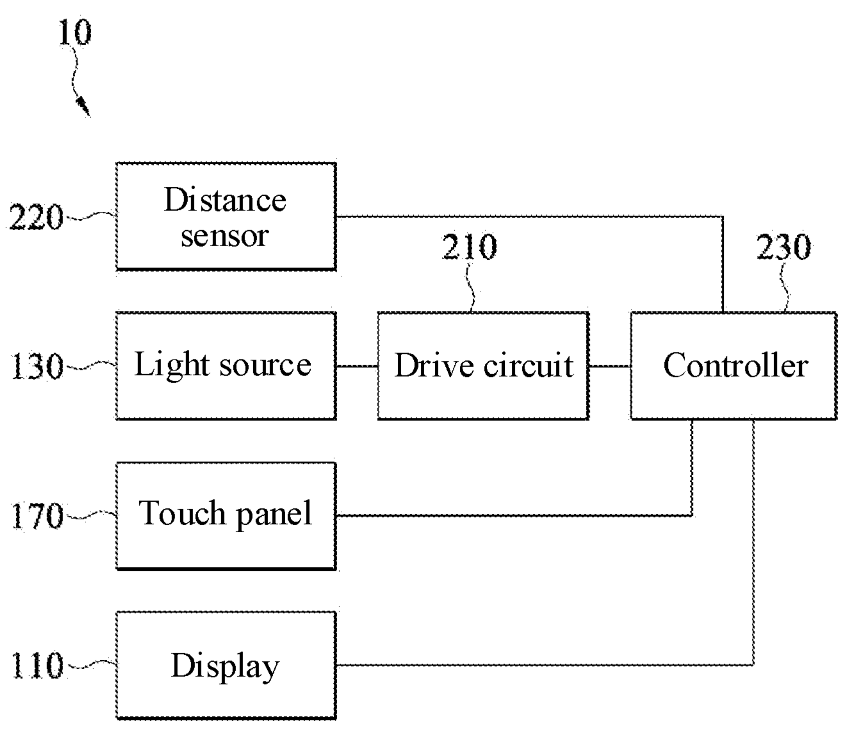
FIG. 13 is a functional block diagram of a self-sterilizing display device.

In some embodiments, referring to FIG. 13, the self-sterilizing display device 10 may further include a drive circuit 210, a distance sensor 220, and a controller 230. The drive circuit 210 is coupled to the light source 130. The controller 230 is coupled to the distance sensor 220, the drive circuit 210, the touch panel 170, and the display 110. The controller 230 is configured to control the operations of the drive circuit 210, the touch panel 170, and the display 110. The distance sensor 220 senses the front of the self-sterilizing display device 10. When the distance sensor 220 senses that there is no one in front of the self-sterilizing display device 10, the controller 230 activates the drive circuit 210 to allow the drive circuit 210 to drive the light source 130 (that is, to allow the light source 130 to emit UV light Luv).

In some embodiments, referring to FIG. 13, FIG. 14, FIG. 15, and FIG. 16, the controller 230 may be disposed on a circuit board 240. In an example, the drive circuit 210 may be disposed on the circuit board 240. In another example, the drive circuit 210 may be disposed on a substrate of the light source 130 together with the light-emitting unit 134.

Figure 14:
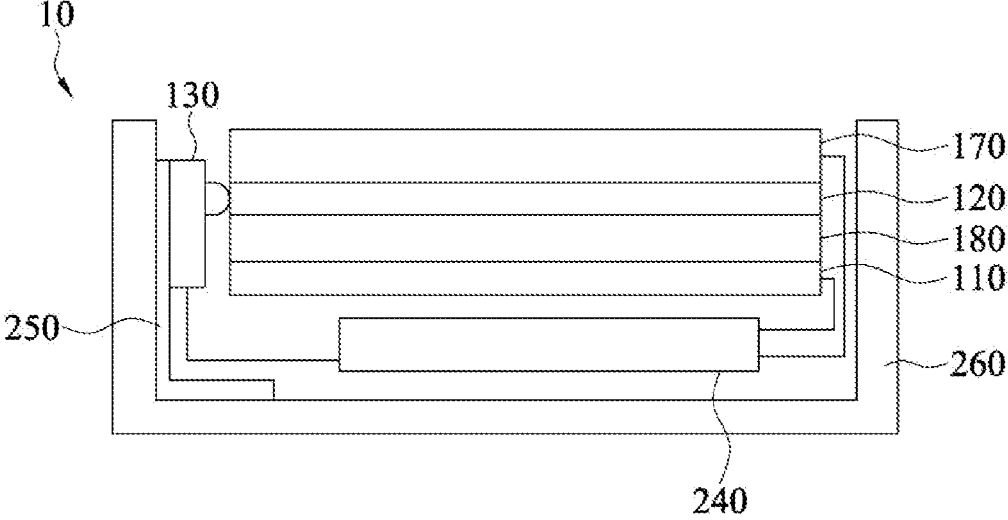
FIG. 14 is a cross sectional view of a self-sterilizing display device assembled with a housing according to some implementations.
Figures 15, 16:
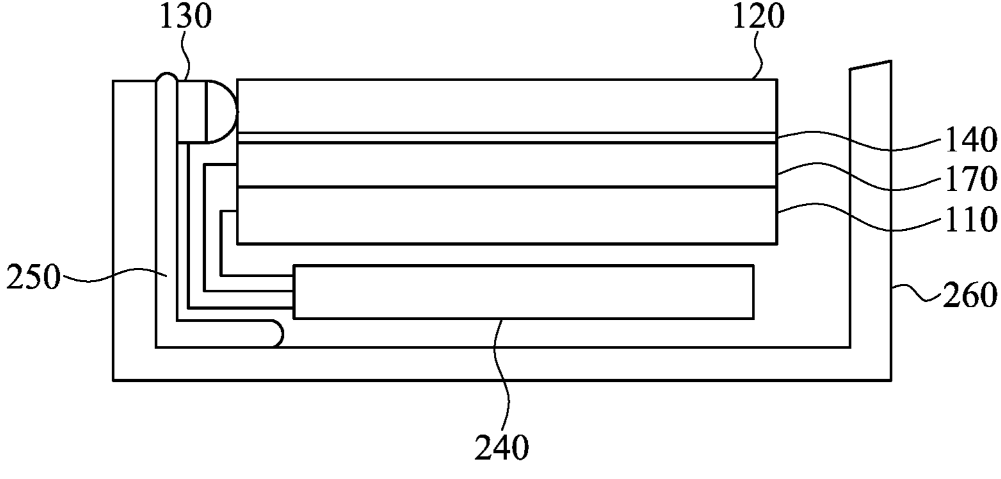
FIG. 15 is a cross sectional view of a self-sterilizing display device assembled with a housing according to some other implementations.
FIG. 16 is a cross sectional view of a self-sterilizing display device assembled with a housing according to still some other implementations.

In some embodiments, referring to FIG. 14, FIG. 15, and FIG. 16, the self-sterilizing display device 10 may further include a heat sink 250 and a housing 260. The foregoing components (such as the display 110, the light-incident layer 120, the light source 130, and the turning layer 140 shown in an example, or the display 110, the light-incident layer 120, the light source 130, the touch panel 170, and the transparent protective layer 180 shown in another example) are accommodated in an accommodation space of the housing 260. The upper surface 10*a* (that is, the upper surface of the component on top of the components, such as the upper surface 120*a* of the light-incident layer 120 shown in an example, or the upper surface 170*a* of the touch panel 170 shown in another example) of the self-sterilizing display device 10 is embedded at an opening (that is, an opening of the accommodation space) of the housing 260. The heat sink 250 is coupled to the housing 260 and the light source 130, and can conduct heat generated by the light source 130 to the housing 260. For example, one surface of the heat sink 250 is attached to the light source 130, and the other surface of the heat sink 250 is attached to a wall surface of the housing 260 (such as an inner wall of the housing 260).

In some application examples, the self-sterilizing display device 10 of any embodiment may be applied to a notebook computer (for example, as a display component), so that it can perform self-sterilization (that is, sterilization on the screen) after the display component and a host component of the notebook computer are closed and/or sterilize a keyboard on the host component. In some other application examples, the self-sterilizing display device 10 of any embodiment may be applied to a vehicle (for example, as an in-vehicle display), so that it can perform self-sterilization (that is, sterilization on the in-vehicle display) after the vehicle is turned off. In still some other application examples, the self-sterilizing display device 10 of any embodiment may be applied to a medical display or electronic whiteboard, so that it can perform self-sterilization (that is, sterilization on the medical display or electronic whiteboard) when not in use. In some further application examples, the self-sterilizing display device 10 of any embodiment may be applied to objects thereon for sterilization. For example, tableware is disposed on a screen of a hand-held device with a sterilization function turned on, or a surface to be sterilized is covered by the screen of the hand-held device with the sterilization function turned on.

Based on the above, the self-sterilizing display device 10 of any embodiment is suitable for a thin or narrow-bezel display device, and is suitable for use with or without a touch panel 170. Herein, the self-sterilizing display device 10 utilizes the built-in UV light Luv source 130 to irradiate the light-incident layer 120 with UV light Luv from the inside to the outer surface 10*a*, thereby achieving comprehensive and strong sterilization of the outer surface 10*a* of the self-sterilizing display device 10. In addition, the self-sterilizing display device 10 also avoids or reduces the incidence of UV light Luv to the display 110 below, causing damage to the display 110, by arranging at least one line of defense below the light-incident layer 120. In this way, the self-sterilizing display device 10 not only has a self-sterilization function, but also does not significantly reduce the service life of the display 110 due to long-term exposure to UV light Luv. In some embodiments, the self-sterilization function of the self-sterilizing display device 10 may be activated in a passive sterilization manner. That is, the self-sterilizing display device 10 turns on the UV light Luv source 130 for sterilization only when no one is around. In some embodiments, the self-sterilizing display device 10 has a warning function, which can emit fluorescent light as a warning when the surface is sterilized.

What is claimed is:

1. A self-sterilizing display device, comprising:

a display;

a light-incident layer, disposed above the display;

a light source, disposed at a periphery of the light-incident layer, a light-emitting surface of the light source facing to the light-incident layer, configured to emit a UV light toward the light-incident layer for sterilizing an outer surface of the self-sterilizing display device by irradiation; and a transparent protective layer, disposed between the light-incident layer and the display, configured to filter out the UV light;

wherein the light source comprises a plurality of light-emitting units located between a plurality of chip-on-film packaging wires of the display.

2. The self-sterilizing display device according to claim 1, further comprising:

a housing; and a heat sink, having one surface attached to the light source, and the other surface attached to a wall surface of the housing.

3. The self-sterilizing display device according to claim 1, further comprising:

a touch panel, disposed above the display.

4. The self-sterilizing display device according to claim 1, wherein the light-incident layer is a light guide plate.

5. The self-sterilizing display device according to claim 4, further comprising a touch panel disposed above the light-incident layer, wherein the transparent protective layer comprises a first adhesive layer, a lower surface of the light guide plate is attached to an upper surface of the display by the first adhesive layer, and a plurality of light-absorbing particles configured to absorb the UV light are distributed inside the first adhesive layer.

6. The self-sterilizing display device according to claim 4, further comprising a touch panel disposed above the light-incident layer, wherein the transparent protective layer comprises a first adhesive layer and a specular reflective layer, the specular reflective layer is formed on an upper surface of the display, a lower surface of the light guide plate is attached to the specular reflective layer by the first adhesive layer, and a plurality of light-absorbing particles configured to absorb the UV light are distributed inside the first adhesive layer.

7. The self-sterilizing display device according to claim 4, wherein the lower surface of the light guide plate has a plurality of microstructures arranged in random order.

8. The self-sterilizing display device according to claim 4, wherein the lower surface of the light guide plate has a plurality of microstructures corresponding to a black matrix configuration of the display.

9. The self-sterilizing display device according to claim 1, wherein the light-incident layer is an adhesive layer.

10. The self-sterilizing display device according to claim 9, further comprising a touch panel attached to the transparent protective layer by the adhesive layer, wherein the refractive index of the adhesive layer is greater than the refractive index of a non-patterned region of the touch panel.

11. The self-sterilizing display device according to claim 1, wherein the light-incident layer is a hollow spacer layer.

12. The self-sterilizing display device according to claim 11, further comprising:

a touch panel disposed above the hollow spacer layer, wherein the hollow spacer layer comprises a space and a reflector, the space is between the display and the touch panel, and the reflector and the light source surround the space.

13. The self-sterilizing display device according to claim 11, further comprising:

a prism, disposed above the light-emitting surface of the light source.

14. The self-sterilizing display device according to claim 11, further comprising:

a touch panel, disposed above the light-incident layer; and a light shielding layer, disposed above the touch panel opposite to the reflector and the light source.

15. The self-sterilizing display device according to claim 14, wherein each of an upper surface of the touch panel and an upper surface of the light shielding layer has a plasma coating film transmissible by the UV light.

16. The self-sterilizing display device according to claim 15, wherein the plasma coating film has a transmittance greater than 60% in a wavelength range of below 380 nm.

17. The self-sterilizing display device according to claim 3, wherein an upper surface of the touch panel has a plasma coating film transmissible by the UV light.

18. The self-sterilizing display device according to claim 17, wherein the plasma coating film has a transmittance greater than 60% in a wavelength range of below 380 nm.

19. The self-sterilizing display device according to claim 1, further comprising:

a fluorescent pattern, disposed between the light-incident layer and the display, for being excited by the UV light to emit fluorescent light.

20. The self-sterilizing display device according to claim 1, further comprising:

a drive circuit, coupled to the light source;

a distance sensor configured to sense the front of the self-sterilizing display device; and a controller, coupled to the distance sensor, the drive circuit, and the display, and configured for activating the drive circuit to drive the light source when the distance sensor senses that there is no one in front of the self-sterilizing display device.

* * * * *